US007852468B2

(12) United States Patent
DiFoggio

(10) Patent No.: US 7,852,468 B2
(45) Date of Patent: Dec. 14, 2010

(54) FIBER OPTIC REFRACTOMETER

(75) Inventor: Rocco DiFoggio, Houston, TX (US)

(73) Assignee: Baker Hughes Incorporated, Houston, TX (US)

(*) Notice: Subject to any disclaimer, the term of this patent is extended or adjusted under 35 U.S.C. 154(b) by 0 days.

(21) Appl. No.: 11/956,945

(22) Filed: Dec. 14, 2007

(65) Prior Publication Data
US 2009/0153845 A1 Jun. 18, 2009

(51) Int. Cl.
*G01N 21/41* (2006.01)
*G01N 21/00* (2006.01)
*G01V 5/08* (2006.01)

(52) U.S. Cl. .................. 356/133; 356/436; 250/269.1

(58) Field of Classification Search ........... 356/432, 356/435–436, 445, 410, 417, 128–137; 250/269.1, 250/256, 339.11, 341.8; 73/152.01, 152.02, 73/152.08, 152.55, 597
See application file for complete search history.

(56) References Cited

U.S. PATENT DOCUMENTS

| | | | |
|---|---|---|---|
| 4,437,761 A | 3/1984 | Kroger et al. | |
| 4,699,511 A | 10/1987 | Seaver | |
| 4,781,458 A * | 11/1988 | Angel et al. | 356/301 |
| 4,844,608 A * | 7/1989 | Smith | 356/136 |
| 4,859,844 A | 8/1989 | Herman et al. | |
| 4,994,671 A | 2/1991 | Safinya et al. | |
| 5,005,005 A | 4/1991 | Brossia et al. | |
| 5,303,775 A | 4/1994 | Michaels et al. | |
| 5,663,559 A * | 9/1997 | Auzerais et al. | 250/269.1 |
| 5,663,790 A | 9/1997 | Ekstrom et al. | |
| 5,831,743 A | 11/1998 | Ramos et al. | |
| 6,184,980 B1 | 2/2001 | Brown et al. | |
| 6,223,822 B1 * | 5/2001 | Jones | 166/250.05 |
| 6,233,746 B1 | 5/2001 | Skinner | |
| 6,343,507 B1 * | 2/2002 | Felling et al. | 73/152.19 |
| 6,388,251 B1 | 5/2002 | Papanyan | |
| 6,507,401 B1 * | 1/2003 | Turner et al. | 356/436 |
| 6,678,050 B2 * | 1/2004 | Pope et al. | 356/435 |
| 6,683,681 B2 | 1/2004 | DiFoggio et al. | |
| 6,975,388 B2 | 12/2005 | Frot | |
| 6,997,055 B2 | 2/2006 | DiFoggio | |
| 7,016,026 B2 | 3/2006 | DiFoggio et al. | |

(Continued)

FOREIGN PATENT DOCUMENTS

JP 08219989 A1 8/1996

OTHER PUBLICATIONS

S.T. Huntington, et al. "Evanescent field characterisation of tapered optical fibre sensors in liquid environments using near field scanning optical microscopy and atomic force microscopy". IEE Proc.-Optoelectron., vol. 146, No. 5, Oct. 1999. pp. 239-243.

(Continued)

*Primary Examiner*—Sang Nguyen
(74) *Attorney, Agent, or Firm*—Cantor Colburn LLP

(57) ABSTRACT

A downhole refractometer apparatus and method include a light source, an optical fiber that receives light emitted from the light source and a fluid cell that receives a downhole fluid. A metalloid interface member is disposed to provide an interface with the downhole fluid in the fluid cell, and a light detecting device detects a light reaction at the metalloid interface member, the downhole fluid property being estimable at least in part based on the light reaction.

21 Claims, 5 Drawing Sheets

Comparison of Silicon-Fluid to Sapphire-Fluid Reflections

U.S. PATENT DOCUMENTS

| | | | |
|---|---|---|---|
| 7,028,543 | B2 | 4/2006 | Hardage et al. |
| 7,099,015 | B2 | 8/2006 | Melnyk |
| 7,183,778 | B2 * | 2/2007 | Homan et al. ............... 324/693 |
| 7,319,523 | B2 | 1/2008 | Chiarello et al. |
| 7,330,262 | B2 * | 2/2008 | Siepmann et al. ........... 356/441 |
| 7,418,865 | B2 * | 9/2008 | Griffiths et al. ............... 73/597 |
| 7,497,256 | B2 * | 3/2009 | DiFoggio et al. ............ 166/264 |
| 7,498,567 | B2 * | 3/2009 | Brady ........................ 250/256 |
| 2003/0193662 | A1 | 10/2003 | Difoggio et al. |
| 2006/0175547 | A1 * | 8/2006 | DiFoggio et al. ......... 250/269.1 |
| 2007/0068242 | A1 * | 3/2007 | DiFoggio ................. 73/152.55 |
| 2007/0268479 | A1 | 11/2007 | Downey |
| 2008/0043242 | A1 | 2/2008 | Emmerson et al. |

OTHER PUBLICATIONS

Masoud Ghandehari, et al. "An Evanescent-Field Fiber Optic Sensor for PH Monitoring in Civil Infrastructure". 15th ASCE Engineering Mechanics Conference. Jun. 2-5, 2002, Columbia University, New York, NY.

Wenqi Gong, et al. "The influence of dissolved gas on the interactions between surfaces of different hydrophobicity in aqueous media". Part II. A spectroscopic study. Phys. Chem. Chem. Phys., 1999, 1, 2799-2803.

J.-P. Conzen, et al. "Characterization of a Fiber-Optic Evanescent Wave Absorbance Sensor for Nonpolar Organic Compounds". Applied Spectroscopy, vol. 47, No. 6, 1993. pp. 753-754.

Rocco DiFoggio, "Evanescent Wave Downhole Fiber Optic Spectrometer". U.S. Appl. No. 12/354,117, filed Jan. 15, 2009.

International Search Report and Written Opinion, Mailed Oct. 12, 2009, International Application No. PCT/US2008/086432, International Search Report 5 pages, Written Opinion 9 pages.

* cited by examiner

FIBER OPTIC REFRACTOMETER

BACKGROUND

1. Technical Field

The present disclosure generally relates to well bore tools and in particular to apparatus and methods for estimating downhole fluid properties.

2. Background Information

Oil and gas wells have been drilled at depths ranging from a few thousand feet to as deep as five miles. A large portion of the current drilling activity involves directional drilling that includes drilling boreholes deviated from vertical by a few degrees up to horizontal to increase the hydrocarbon production from earth subterranean formations.

Information about the subterranean formations traversed by the borehole may be obtained by any number of techniques. Some techniques used to obtain formation information include obtaining one or more core samples of the subterranean formations and obtaining one or more fluid samples produced from the subterranean formations. These samplings are collectively referred to herein as formation sampling. Modern fluid sampling includes various downhole tests and sometimes fluid samples are retrieved for surface laboratory testing.

One test that may be performed on downhole fluid includes estimating the refractive index of the downhole fluid using a light source emitting a light to a fluid interface and then measuring an intensity of light reflected or refracted at the interface. Changes in refractive index can be used to monitor fluid sample cleanup from mud-filtrate-contaminated fluid to nearly pure formation fluid. Also, fluid refractive index correlates to fluid density and polarizability.

SUMMARY

The following presents a general summary of several aspects of the disclosure in order to provide a basic understanding of at least some aspects of the disclosure. This summary is not an extensive overview of the disclosure. It is not intended to identify key or critical elements of the disclosure or to delineate the scope of the claims. The following summary merely presents some concepts of the disclosure in a general form as a prelude to the more detailed description that follows.

Disclosed is a downhole refractometer apparatus for estimating a downhole fluid property. The apparatus includes a light source, an optical fiber that receives light emitted from the light source and a fluid cell that receives a downhole fluid. A metalloid interface member is disposed to provide an interface with the downhole fluid in the fluid cell, and a light detecting device detects a light reaction at the metalloid interface member, the downhole fluid property being estimable at least in part based on the light reaction.

A method for estimating a downhole fluid property includes emitting a light from a light source, conveying the emitted light in an optical fiber toward a metalloid interface member disposed to provide an interface with a downhole fluid in a fluid cell, detecting a light reaction at the metalloid interface member using a light detecting device, and estimating the downhole fluid property at least in part using the detected light reaction.

Another aspect of the disclosure is a refractometer with downhole calibration that includes a light source that emits at least two wavelengths of light to an optical fiber. A fluid cell receives a downhole fluid and a metalloid interface member is disposed to provide an interface with the downhole fluid in the fluid cell, the metalloid interface member reflecting a first wavelength of the at least two wavelengths to a return optical fiber and transmitting a second wavelength of the at least two wavelengths to the downhole fluid, at least a fraction of the second wavelength being reflected at the fluid/metalloid interface and proceeding on to the return optical fiber. A light detecting device detects the first wavelength and the reflected fraction of the second wavelength, the detected first wavelength being indicative of a light source characteristic and the detected fraction of the second wavelength being indicative of a downhole fluid characteristic.

A method for calibrating a refractometer downhole includes emitting at least two wavelengths of light from a light source to an optical fiber and receiving a downhole fluid in a fluid cell, a metalloid interface member being disposed to provide an interface with the downhole fluid in the fluid cell. The method further includes reflecting a first wavelength of the at least two wavelengths to a return optical fiber, transmitting a second wavelength of the at least two wavelengths to the downhole fluid and reflecting at least a fraction of the second wavelength at the fluid and to the return optical fiber. The first wavelength and the reflected fraction of the second wavelength are detected with a light detecting device, the detected first wavelength being indicative of a light source characteristic and the detected fraction of the second wavelength being indicative of a downhole fluid characteristic. The refractometer is calibrated in-situ using the light source characteristic and the downhole fluid characteristic.

BRIEF DESCRIPTION OF THE DRAWINGS

For a detailed understanding of the present disclosure, reference should be made to the following detailed description of the several non-limiting embodiments, taken in conjunction with the accompanying drawings, in which like elements have been given like numerals and wherein.

DESCRIPTION OF EXEMPLARY EMBODIMENTS

The present disclosure uses terms, the meaning of which terms may aid in understanding of the discussion herein. As used herein, the terms metalloid or semimetal are used synonymously and include those elemental materials located along the line between the metals and nonmetals in the periodic table. The metalloids include boron, silicon, germanium, arsenic, antimony, tellurium, and polonium.

Figure 1:
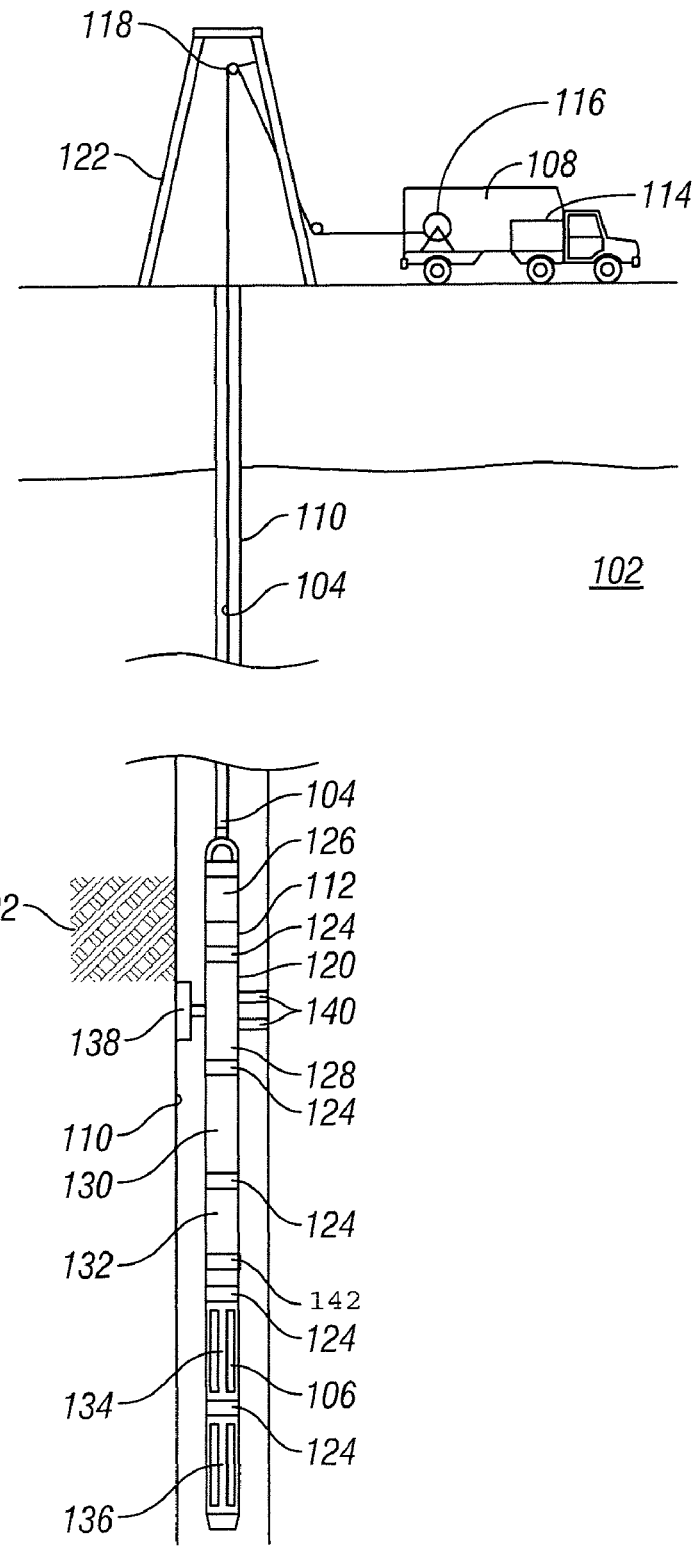
FIG. 1 is an exemplary wireline system according to several embodiments of the disclosure.

FIG. 1 schematically illustrates a non-limiting example of a wireline apparatus according to several disclosed embodiments. In the example shown, a well borehole 110 traverses several subterranean formations 102. The well borehole 110 will typically be filled or at least partially filled with a fluid mixture of including various gases, water, drilling fluid, and formation fluids that are indigenous to the subterranean formations penetrated by the well borehole. Such fluid mixtures are referred herein to as "well borehole fluids". The terms "connate fluid" and "natural fluid", as used herein, refer to fluids naturally existing in or extracted from the subterranean formations 102 and exclusive of any substantial mixture or contamination by fluids not naturally present in the formation, such as drilling fluid.

A formation evaluation tool 120 is conveyed in the well borehole 110 using a wireline 104. Wire line deployment and retrieval may be performed by a powered winch carried by a service truck 108, for example. The wireline 104 typically is an armored cable that carries data and power conductors for providing power to the formation evaluation tool 120 and to provide two-way data communication between a tool processor 112 and a controller 114 that may be carried by the service truck 108. The wireline 104 typically is carried from a spool 116 over a pulley 118 supported by a derrick 122. The spool 116 may be carried by the truck 108 as shown for on-land operations, by an offshore rig for underwater operations or by any other suitable mobile or fixed supporting structure. The controller 114 may include a processor, such as within a computer or a microprocessor, data storage devices, such as solid state memory and magnetic tapes, peripherals, such as data input devices and display devices, and other circuitry for controlling and processing data received from the formation evaluation tool 120. The surface controller 114 may further include one or more computer programs embedded in a computer-readable medium accessible to the processor in the controller 114 for executing instructions contained in the computer programs to perform the various methods and functions associated with the processing of the data from the formation evaluation tool 120. It may also be useful in production logging to identify the fluid phases flowing into the wellbore and to identify which phases (gas, water, oil) are being produced from a particular perforation in the casing.

The formation evaluation tool 120 lower portion may include an assembly of several tool segments that are joined end-to-end by threaded sleeves or mutual compression unions 124. An assembly of tool segments appropriate for the present invention may include a power unit 126 that may include one or more of a hydraulic power unit, an electrical power unit or an electro-mechanical power unit. In the example shown, a formation fluid extractor 128 is coupled to the formation evaluation tool 120 below the power unit 126. A large displacement volume motor/pump unit 130 may be provided below the formation fluid extractor 128 for line purging. A similar motor/pump unit 132 having a smaller displacement volume may be included in the tool in a suitable location, such as below the large volume pump, for quantitatively monitoring fluid received by the formation evaluation tool 120. One or more sample tank magazine sections 134 may be included for retaining fluid samples from the small volume pump 132. Each magazine section 134 may have several fluid sample tanks 136. In several embodiments to be described in further detail later, the formation evaluation tool 120 includes a downhole refractometer 142. The refractometer may be used in either the while-drilling embodiments or in the wireline embodiments.

The formation fluid extractor 128 comprises an extensible suction probe 138 that is opposed by bore wall feet 140. Both, the suction probe 138 and the opposing feet 140 may be hydraulically or electro-mechanically extendable to firmly engage the well borehole wall. Construction and operational details of a suitable non-limiting fluid extraction tool 128 are more described by U.S. Pat. No. 5,303,775, the specification of which is incorporated herein by reference.

Figure 2:
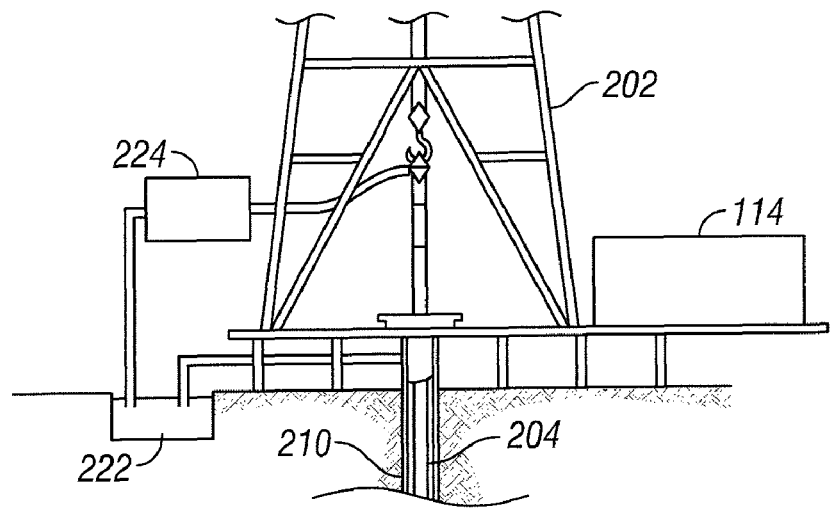
FIG. 2 illustrates a non-limiting example of a while-drilling system according to the disclosure.
Figure 2:
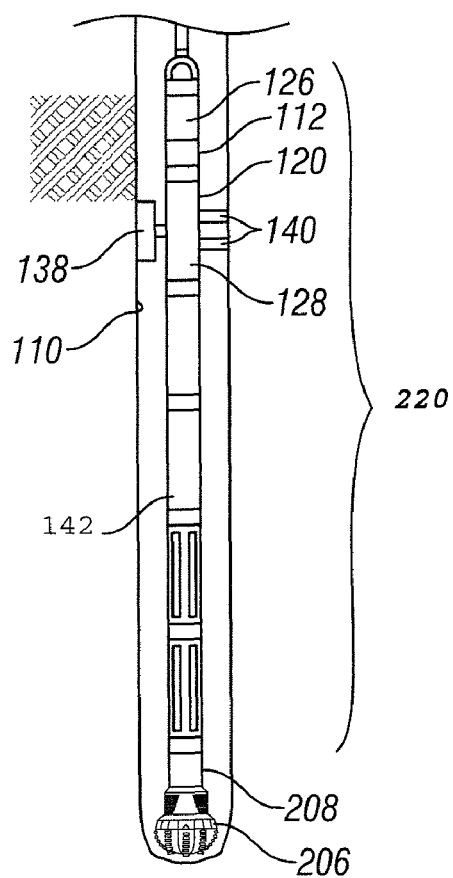

FIG. 2 schematically illustrates a non-limiting example of a drilling system 200 in a measurement-while-drilling (MWD) arrangement according to several non-limiting embodiments of the disclosure. A derrick 202 supports a drill string 204, which may be a coiled tube or drill pipe. The drill string 204 may carry a bottom hole assembly (BHA) 220 and a drill bit 206 at a distal end of the drill string 204 for drilling a borehole 110 through earth formations.

Drilling operations according to several embodiments may include pumping drilling fluid or "mud" from a mud pit 222, and using a circulation system 224, circulating the mud through an inner bore of the drill string 204. The mud exits the drill string 204 at the drill bit 206 and returns to the surface through an annular space between the drill string 204 and inner wall of the borehole 110. The drilling fluid is designed to provide a hydrostatic pressure that is greater than the formation pressure to avoid blowouts. The pressurized drilling fluid may further be used to drive a drilling motor 208 and may provide lubrication to various elements of the drill string 204.

In the non-limiting embodiment of FIG. 2, the BHA 220 includes a formation evaluation tool 120 substantially similar to the formation evaluation tool 120 described above and shown in FIG. 1.

The while-drilling formation evaluation tool 120 may carry a fluid extractor 128 including an extendable suction probe 138 and opposing feet 140. In several embodiments to be described in further detail later, the formation evaluation tool 120 includes a downhole refractometer 142. The refractometer 142 may be used in either the while-drilling embodiments or in the wireline embodiments.

Figure 3:
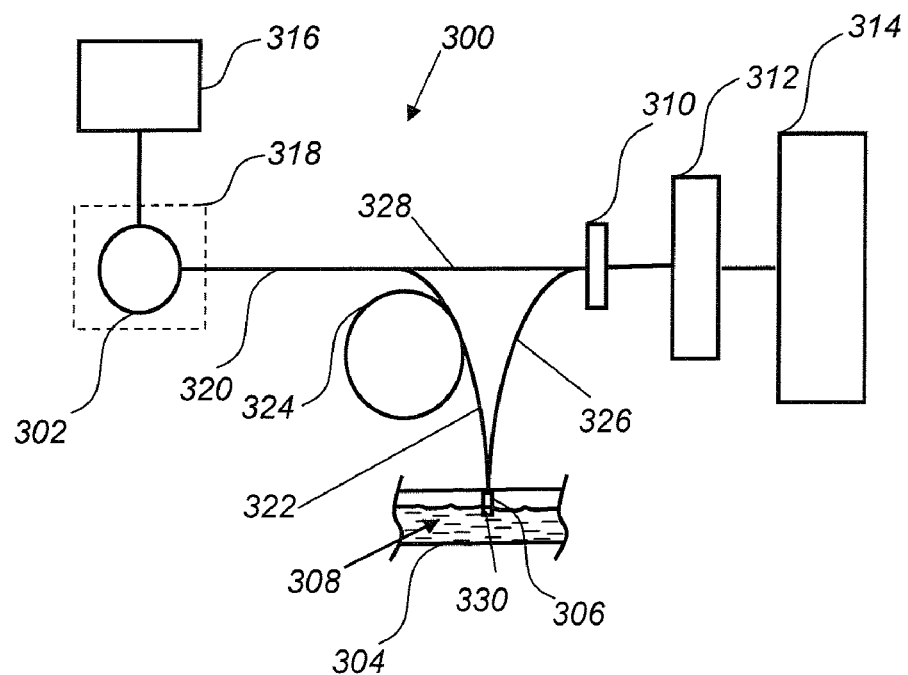
FIG. 3 is a non-limiting example of a downhole refractometer according to several embodiments of the disclosure.

FIG. 3 schematically illustrates a non-limiting example of a downhole fluid test device according to the disclosure. In one or more embodiments, the downhole fluid test device may include a refractometer 300 that may be incorporated into any of several wireline or while drilling tools, including the formation evaluation tool 120 described above and shown as a downhole refractometer 142 in FIGS. 1 and 2.

The downhole refractometer 300 in the example shown includes a light source 302. In several embodiments, the light source 302 may comprise an array of light sources. The light source 302 emits light toward a formation fluid cell 304 via one or more optical fibers 320. In the example of FIG. 3, the optical fibers 320 include a source optical fiber 322 leading from the light source to the fluid cell 304 and an optional delay loop 324 is shown incorporated into the source optical fiber 322 leading to the fluid cell 304. The delay loop 324, when used, may be located in any suitable optical fiber section. The delay loop provides the optical fiber section with a length that is longer than the section without the delay loop 324. In several embodiments, the section having the delay loop lengthens the section having the delay loop to delay light detection for light traveling in the section having the delay loop.

A return optical fiber 326 couples the fluid cell 304 to a photodetector 310 and an optional direct source optical fiber 328 may lead directly from the light source 302 to the photodetector 310 to convey light having the intensity as emitted from the source 302 to the detector 310. The source optical fiber 322 leading to the fluid cell 304 and the return optical fiber 326 leading from the fluid cell 304 are coupled with a tip member 306 in contact with fluid 308 in the fluid cell 304. In several embodiments, the tip member 306 includes a metalloid interface 330. The metalloid interface 330 may be layered, deposited or connected to the tip member 306 such that the metalloid interface 330 portion of the top member 306 contacts fluid 308 in the fluid cell 304.

The photodetector 310 may be used to receive light emitted from the light source 302 after the light interacts with the fluid 308 via the return optical fiber 326. In one or more embodiments, the photodetector 310 comprises a single broadband photodetector responsive to light emitted from the light source 302 and/or light reflected at the fluid-metalloid tip interface. In other non-limiting embodiments, the photodetector 310 comprises a dual-layer photodetector responsive to light emitted from the light source 302 and/or light reflected at the fluid-metalloid tip interface. A suitable dual-layer photodetector is a dual-layer Si and InGaAs photodetector such as the Dual Sandwich photodetector available from Thor Labs, Inc. located in Newton, N.J. The photodetector 310 provides an output signal indicative of the light received at the photodetector 310. In some cases, the photodetector output signal may be an analog electrical signal, so an analog-to-digital converter 312 may be used to convert the photodetector output signal into a digital signal that is received by a downhole controller 314, 316 or by a surface controller 114. The light emitted from the light source 302 may be modulated by a processor within the same controller 314 that receives the photodetector output or by a modulator in a separate controller 316. In the example shown, one modulator/controller 314 is coupled to the photodetector 310 and a second modulator/controller 316 is coupled to the light source 302. These controllers may be implemented as a single controller without departing from the scope of the disclosure. In other embodiments, the controller or controllers 314, 316 may be located at the surface of the well borehole as described above and show in FIGS. 1 and 2 at 114 using any of several communication methods. Cooling one or more of these downhole components may be accomplished using a cooling device 318. The cooling device 318 used may be any number of devices, examples of which include thermal-electric, thermo-tunneling, sorption cooling, evaporators, and Dewar. Cooling is optional where components selected are compatible with the downhole temperature environment.

Cooling may be applied where a component operating temperature is lower than the downhole environment and/or were cooling may enhance performance of the component. In several embodiments, the light source 302 is compatible with the downhole temperature environment and the cooling device 318 is optional. Cooling in some cases could improve photodetector signal-to-noise ratio and increase laser brightness where the light source 302 comprises one or more lasers.

The several non-limiting examples of refractometer tools disclosed herein provide a small, lightweight, fiber-optic downhole refractometer that has substantially higher resolution than conventional refractometers. Moreover, the refractometer 300, 142 provides in-situ calibration capability. The refractive index of a fluid is estimated by measuring the fraction of light that is reflected at the interface. Using the optical fibers 320 to convey the light provides a device that can be made small and lightweight. Using optical fibers also provides the ability to use an array of sensors, each of which can monitor a different location in a fluid or fluid mixture. The metalloid interface 330 provides a layer of very high index material (such as the semiconductor, semimetals silicon or germanium). Using a metalloid interface provides an increased reflected signal and improves the refractive index resolution for any wavelength longer than the bandgap.

In several examples, the metalloid interface 330 may be more than about 10-20 wavelengths thick. In this manner, the metalloid interface will operate like a mirror for the shorter wavelengths. In one embodiment, mirror-like reflections, which occur for short wavelength photons, can be used for calibrating the source intensity. Silicon has an added advantage of being an almost non-reactive and non-stick surface so it is resistant to both corrosion by the fluid and fouling by deposits from the fluid. Germanium is also fairly non-reactive chemically. Silicon and germanium are also semiconductors so they have a bandgap and operate as a mirror to photons with energy greater than the bandgap and operate as a transparent window to photons with energy less than the bandgap energy. Silicon for example changes from a mirror to a window at wavelengths longer than about 1100 nm and germanium changes from a mirror to a window at wavelengths longer than about 1800 nm. In several embodiments, the downhole refractometer 300 may be calibrated in-situ using a light source generating both short and long wavelengths and using a metalloid interface with mirror/window properties.

In several embodiments, the light source 302 may include one or more broadband light sources such as an incandescent light source along with an optical filter to provide selected wavelengths, or the light source 302 may include one more light-emitting diodes (LED). The light source may also use one or more laser diodes. In other embodiments, the downhole refractometer 300 may include one or more light sources 302 that include a combination of light source types.

The non-limiting example of FIG. 3 illustrates a delay line embodiment. The light source may include a light emitting diode (LED) or a laser diode to emit a light of a selected wavelength. The optical fiber 320 may be configured as a Y-branch fiber as shown with the delay loop 324 positioned in the source optical fiber 322 leading to the fluid cell 304. In this embodiment, a single photodetector 310 is used to receive light from both the direct source optical fiber 328 and the return optical fiber 326. The use of a delay loop allows for distinguishing the source light conveyed via the direct source optical fiber and the return light conveyed via the return optical fiber 326 even though a common wavelength light is emitted from the light source 302. In this manner, the source intensity is detected at one time window and the reflected intensity is detected as a second (delayed) time window. Embodiments that allow for simultaneous detection of the source and reflection intensity are also within the scope of the disclosure.

Some embodiments may be used as a multi-wavelength implementation as mentioned earlier for mirror/window examples. An incandescent light and dual-bandpass filter may be used as a light source 302 to generate two selected wavelengths. Alternatively, dual wavelength diodes or laser diodes may be used. The dual wavelength light may be conveyed via the optical fiber 320 to a silicon or germanium tip immersed in the fluid 308 within the fluid cell 304. A dual-layer photodetector as described above may be used to detect light reflected at the fluid-tip interface. In one embodiment, the two wavelengths include a short wavelength light and a long wavelength light, where the short wavelength light is a light having an energy less than the bandgap of the metalloid tip material and the long wavelength light is a light having an energy greater than the bandgap of the metalloid tip material. The optional direct source fiber 328 is not required in the dual-wavelength embodiments.

The dual wavelength photo detector provides a short wavelength detector and a long wavelength detector to simultaneously detect the wavelengths reflected at the fluid-tip interface. When using a fiber having a Si or Ge tip and a Si and InGaAs detector, the Si portion of the detector will detect the higher intensity reflections of the short wavelength light while the InGaAs portion of the detector detects lower intensity reflections of the long wavelength light.

Figure 4:
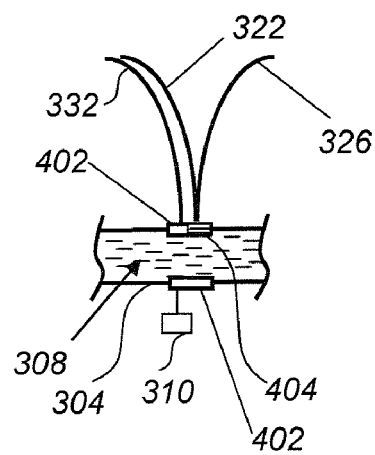
FIG. 4 illustrates an exemplary fluid cell having a window and metalloid fluid interface.

Referring to FIG. 3 and FIG. 4 a fluid cell 400 is shown that may be used with a downhole refractometer substantially similar to the refractometer 300 described above and shown in FIG. 3 and further used with a downhole spectrometer. In the non-limiting example of FIG. 4, a first source optical fiber 322 conveys light from a light source 302 to an optical window 402 having at least a portion that includes a metalloid interface 404 in a fluid cell 304. The fluid cell 304 is filled or partially filled with a downhole fluid 308, and the fluid 308 may be a flowing fluid or a non-flowing fluid. The metalloid interface 404 as described above is positioned as an interface with the fluid 308. A return optical fiber 308 conveys light reflected at the interface to the photodetector 310. In one embodiment, the metalloid interface 404 comprises a layer on the fluid side of a window 402 transparent to the source light in the optical fiber 322. In another embodiment, the metalloid interface 404 extends from the fluid interface to the outer side of the window 402 portion that is coupled to the optical fibers 322, 326.

A second source optical fiber 332 may be Y-coupled to the first source optical fiber 322 to carry source light to a portion of the window 402 that allows the light to be transmitted into the fluid 308, through about 2 mm of the fluid 308 to a second window 304 on an opposite side of the fluid cell 304 to be detected by a photodetector 310. In this manner, the light spectra detected by the second photodetector 310 may be transmitted to a processor in the controller 114, 314, 316 as described above for processing and for estimating the optical properties and content of the fluid 308 in the fluid cell 304.

Figure 5:
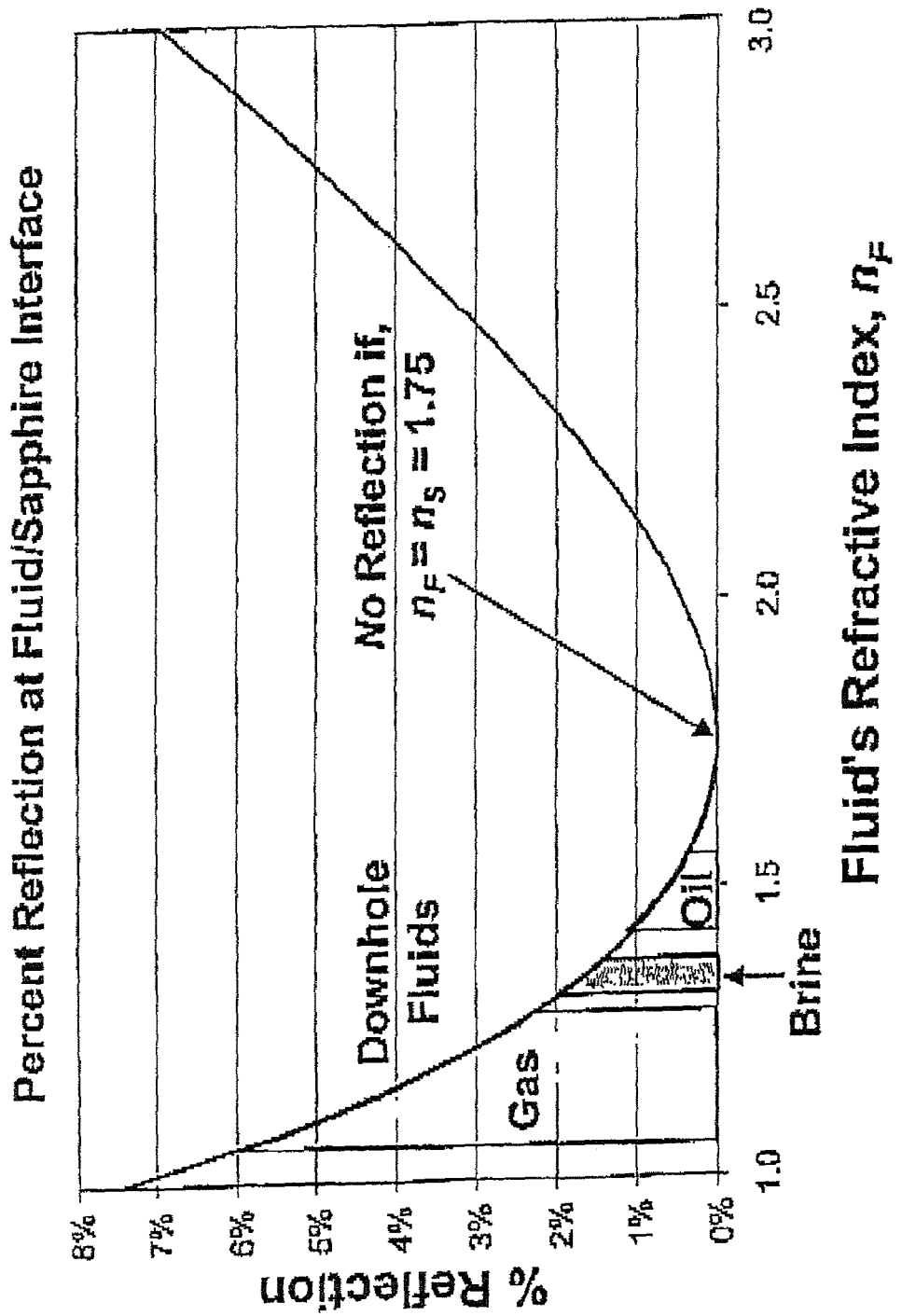
FIG. 5 is a plot of fluid refractive index for a typical sapphire interface.

FIG. 5 is a plot showing the reflection percentage at the interface of a downhole fluid and a typical sapphire window used in some downhole optical fluid analysis tools. The fraction of light R, reflected at a fluid-window interface depends on the ratio of the respective indices, $\eta_F/\eta_W$. Knowing the refractive index of a window $\eta_W$ and measuring R, one can determine the fluid refractive index $\eta_F$ using the relationship of Equation 1.

$$R = \left( \frac{(1 - \eta_{Fluid}/\eta_{Window})^2}{(1 + \eta_{Fluid}/\eta_{Window})^2} \right) \quad \text{Equation 1}$$

The refractive index of sapphire $\eta_S$ is 1.75. The refractive index of a downhole fluid varies depending on the fluid content but it is invariably less than 1.75. There would be no reflection if the fluid's refractive index $\eta_F$ equaled the refractive index of the sapphire window because, in that case, there would be no change in refractive index when crossing the interface.

Figure 6:
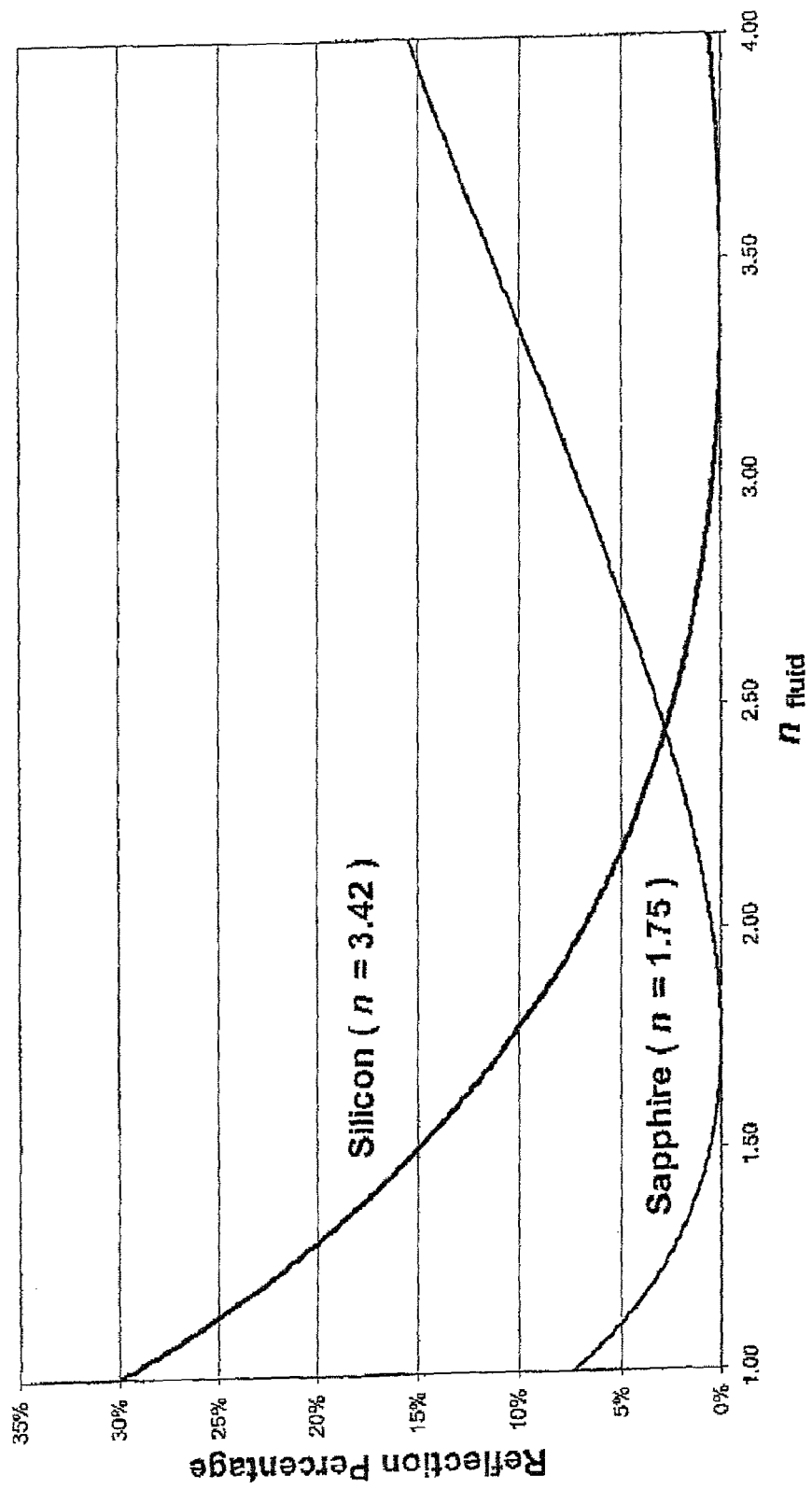
FIG. 6 is a plot to compare the refractive indices of sapphire and silicon fluid interfaces.

FIG. 6 is a plot showing the comparison of a silicon interface and a sapphire interface with a downhole fluid. The plot illustrates that the refractive index of silicon, $\eta_{Si}$=3.42, is much higher than the 1.75 refractive index of a sapphire interface. As a result, the silicon interface is more sensitive to small changes in the fluid refractive index providing information useful in a more precise identification of the fluid composition.

Another advantage of a silicon interface is that a silicon interface provides a smooth surface that is resistant to fouling by downhole fluid deposits. Furthermore, silicon acts as a mirror for light wavelengths shorter than about 1100 nm and is substantially transparent to wavelengths longer than about 1100 nm. This characteristic is useful in the dual-wavelength embodiments described above and shown in FIGS. 3-4 by allowing for measuring incident light in real time for real-time calibration of the tool, whereas the typical tool uses stored incident light information derived from surface laboratory tests. As discussed above, germanium is another exemplary metalloid providing mirror and transparent properties depending on the source light wavelength.

Referring to FIGS. 1-6 and the several embodiments described above, operational examples and a method for estimating downhole fluid properties will be described. In one non-limiting embodiment a light is emitted from a light source to be received by an optical fiber. A fluid cell receives a downhole fluid and a metalloid interface member is disposed to provide an interface between the optical fiber and the downhole fluid in the fluid cell. A light reaction occurring at the metalloid interface member is detected using a light detecting device. Downhole fluid properties may be estimated at least in part by using the detected light reaction.

For a reflection-intensity refractometer, the refractive index is determined by measuring the fraction of light reflected and equation 1 above. Note that the larger the ratio of window to fluid refractive index, the brighter the reflection and the greater the sensitivity to changes in fluid refractive index. Sapphire windows are useful because many crude oils have a refractive index of about 1.50, which is below the 1.74 refractive index of the sapphire window. Sapphire windows provide for a tool with a high resolution (0.001) for reading refractive index of fluids like oil and water. The reflection intensity and the refractive index resolution are greatly increased by using a silicon ($\eta_{Si}$=3.42) or germanium ($\eta_{Ge}$=4.0) layer in direct contact with the fluid as noted in FIGS. 5-6.

In some embodiments, determining the refractive index may be accomplished in conjunction with downhole spectroscopy. When performing downhole spectroscopy, a fluid cell substantially similar to the fluid cell described above and shown in FIG. 4 is used where a source light of wavelength less than 1100 nm is transmitted via a source optical fiber 332 through the window 402 portion not having a metalloid interface, through about 2 mm of fluid sample 308, and then through a second window 402 to a second photodetector 310. In this spectroscopy example, the portion of the incident window 402 having the metalloid interface 404 will reflect the short wavelength incident light, in this case wavelengths shorter than about 1100 nm where the metalloid used is Si. The second source fiber and second photodetector 310 may then be used to measure the visible spectra of the light of wavelengths less than 1100 nm.

Operational examples including in-situ calibration of the refractometer should be evident given the several embodiments described above and shown in FIGS. 1-6. One non-limiting operational calibration example for the downhole refractometer includes using an absolute and continuous reference for calibration. In one example, a Y-branched fiber of unequal lengths is accomplished with a delay line on one branch as described above with reference to FIG. 3 to distinguish a pulse of characteristic source light intensity from a pulse of characteristic reflected light intensity by their different arrival times at a single photodetector. A correction factor is applied to the measured intensities to convert the reflected light intensity to the fraction of light reflected. The correction factor may be obtained by measuring both source and reflected intensities when the metalloid interface is immersed in fluid of known refractive index such as air. The correction factor is substantially a function of the geometry and materials used in the fibers and in the metalloid interface, and is therefore almost independent of temperature. In several embodiments, there is no need for a temperature correction for the loss of photodetector sensitivity with temperature where a single photodetector is used to measure both source and reflected light. In this manner, any drift associated with photodetector equally affects the source and reflection measurements, so the ratio of the measurements remains substantially unaffected.

Another non-limiting example of in-situ calibration includes using a dual bandpass optical filter with a broadband light source and using a photodetector that detects a broad range of wavelengths. In one example, a silicon metalloid fluid interface is used and a photodetector having a Si detecting layer and an InGaAs detecting layer is used. Using these particular materials, the dual bandpass optical filter is selected to block light within a region were the detector Si and InGaAs sensitivities overlap. The overlap region is about 900-1200 nm between Si and InGaAs, so the bandpass filter provides a source emitting light in two narrow bandpass regions, one below 900 nm and one above 1200 nm. Blocking the overlap regions facilitates distinguishing between multiple short wavelengths and long wavelength at the photodetector. Light of wavelength longer than 1100 nm goes through the Si layer and then is detected by the InGaAs layer. In this way, in-situ calibration can be done using the ratio of the short wavelength light reflected directly off silicon fluid interface layer at wavelengths shorter than 1100 nm as a source light characteristic where Si acts as a mirror to the long wavelength light reflected from a fluid-silicon interface at wavelengths longer than 1100 nm as a downhole fluid characteristic where silicon acts as a transparent window. The metalloid interface in another example may be Germanium noting that 1800 nm is the wavelength that divides mirror behavior from window behavior.

The present disclosure is to be taken as illustrative rather than as limiting the scope or nature of the claims below. Numerous modifications and variations will become apparent to those skilled in the art after studying the disclosure, including use of equivalent functional and/or structural substitutes for elements described herein, use of equivalent functional couplings for couplings described herein, and/or use of equivalent functional actions for actions described herein. Such insubstantial variations are to be considered within the scope of the claims below.

Given the above disclosure of general concepts and specific embodiments, the scope of protection is defined by the claims appended hereto. The issued claims are not to be taken as limiting Applicant's right to claim disclosed, but not yet literally claimed subject matter by way of one or more further applications including those filed pursuant to the laws of the United States and/or international treaty.

What is claimed is:

1. An apparatus for estimating a downhole fluid property comprising:
    a light source;
    an optical fiber that receives light emitted from the light source;
    a fluid cell that receives a downhole fluid;
    a metalloid interface member disposed to provide an interface with the downhole fluid in the fluid cell; and
    a light detecting device that detects a light reaction at the metalloid interface member, the downhole fluid property being estimable at least in part based on the light reaction.

2. An apparatus according to claim 1, wherein the metalloid interface member comprises one or more of Si and Ge.

3. An apparatus according to claim 1, wherein the metalloid interface member comprises a metalloid material disposed on a distal end of the optical fiber.

4. An apparatus according to claim 3, wherein the distal end of the optical fiber is disposed within the fluid cell and immersed in the downhole fluid to a selected depth.

5. An apparatus according to claim 1, wherein the fluid cell comprises a window, the metalloid interface member comprising a metalloid material forming at least a portion of the window.

6. An apparatus according to claim 1, wherein the light source includes a broad-band light source and a filter for providing a source light having a selected wavelength.

7. An apparatus according to claim 1, wherein the light source includes a narrow-band light source for providing a source light having a selected wavelength.

8. An apparatus according to claim 1, wherein the light detecting device comprises a dual-layer photodetector responsive to at least two wavelengths of light, wherein a first detected wavelength is indicative of light emitted from the light source and a second detected wavelength is indicative of light interaction with the downhole fluid at the metalloid interface member.

9. An apparatus according to claim 1, wherein the optical fiber includes a first section of optical fiber and a second section of optical fiber coupled to the first section in a Y-coupling arrangement, the first section being longer than the second section and wherein the light detecting device detects light traveling in the second section of optical fiber before detecting light traveling in the first section of optical fiber.

10. An apparatus according to claim 9, wherein one of the first section of the optical fiber and the second section of the optical fiber conveys source light toward the metalloid interface member and the other of the first section of the optical fiber and the second section of the optical fiber conveys source light toward the light detecting device.

11. An apparatus according to claim 10 further comprising a processor that receives a first output signal from the light detecting device indicative of source light intensity and a second output signal indicative of reflected light intensity, the source light intensity and the reflected light intensity being detected by the light detecting device at different times.

12. A method for estimating a downhole fluid property comprising:
    emitting a light from a light source;
    conveying the emitted light in an optical fiber toward a metalloid interface member disposed to provide an interface with a downhole fluid in a fluid cell;
    detecting a light reaction at the metalloid interface member using a light detecting device; and
    estimating the downhole fluid property at least in part using the detected light reaction.

13. A method according to claim 12, wherein the metalloid interface member comprises one or more of Si and Ge and detecting a light reaction comprises detecting a light reflection intensity.

14. A method according to claim 12, wherein the metalloid interface member comprises a metalloid material disposed on a distal end of the optical fiber, the method further comprising immersing the distal end of the optical fiber in the downhole fluid to a selected depth.

15. A method according to claim 12, wherein conveying the emitted light includes conveying the emitted light to a window in the fluid cell, the metalloid interface member comprising a metalloid material forming at least a portion of the window.

16. A method according to claim 12, wherein emitting a light includes emitting a broadband light and filtering the broadband light with a filter to provide a source light having a selected wavelength.

17. A method according to claim 12, wherein emitting a light includes emitting a narrow-band light to provide a source light having a selected wavelength.

18. A method according to claim 12, wherein emitting a light includes emitting at least two wavelengths of light, the light detecting device including a dual-layer photodetector responsive to the at least two wavelengths of light and wherein a first detected wavelength is indicative of light emitted from the light source and a second detected wavelength is indicative of light interaction with the downhole fluid at the metalloid interface member.

19. A method according to claim 12, wherein conveying the emitted light includes conveying the emitted light in a first section of optical fiber and conveying the emitted light in a second section of optical fiber coupled to the first section of optical fiber in a Y-coupling arrangement, the method further comprising:

delaying detecting the light conveyed in the first section by using an optical fiber in the first section that is longer than the second section optical fiber; and detecting light traveling in the second section of optical fiber before detecting light traveling in the first section of optical fiber.

20. A method according to claim 19, wherein one of the first section and the second section conveys source light toward the metalloid interface member and the other of the first section and the section conveys source light toward the light detecting device.

21. A method according to claim 20 further comprising transmitting a first output signal from the light detecting device indicative of source light intensity to a processor and transmitting a second output signal from the light detecting device indicative of reflected light intensity to the processor.

* * * * *